Figure 1:
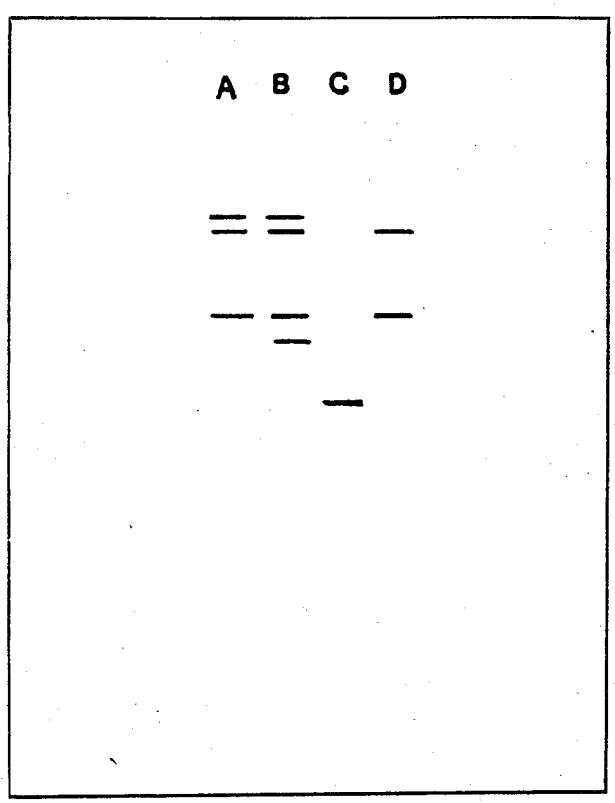

United States Patent [19]

Vandenbergh

[11] Patent Number: 4,593,003
[45] Date of Patent: Jun. 3, 1986

[54] BACTERIAL METHOD AND COMPOSITIONS FOR ISOPRENOID DEGRADATION

[75] Inventor: Peter A. Vandenbergh, Sarasota, Fla.

[73] Assignee: Microlife Technics, Inc., Sarasota, Fla.

[21] Appl. No.: 496,140

[22] Filed: May 19, 1983

[51] Int. Cl.$^4$ .................. C12N 15/00; C12N 1/00; C12N 1/20; C07G 17/00

[52] U.S. Cl. .................. 435/172.3; 435/253; 435/262; 435/267; 435/317; 435/877; 210/611; 210/908; 426/51; 935/29; 935/64; 935/72; 935/56

[58] Field of Search ............ 435/262, 267, 317, 172.1, 435/172.3, 253, 877; 210/611, 908; 426/49, 51, 599

[56] References Cited

U.S. PATENT DOCUMENTS

| | | | |
|---|---|---|---|
| 2,561,072 | 7/1951 | Reich | 426/51 |
| 2,686,146 | 8/1954 | Buswell et al. | 210/611 |
| 4,374,200 | 2/1983 | Olsen . | |
| 4,447,456 | 5/1984 | Hasegawa | 426/51 |

OTHER PUBLICATIONS

McCombie et al, "Pseudomonas Streptomycin-Resistance Transposon Associated with R Plasmid Mobilization", Journal of Bacteriology 155(1) pp. 40-48 (1983).
McCombie, "Genetic and Physical Characterization of TN904", Dissertation Abstracts 43(6) DA8225007 (1982).
Devi et al, "Microbiological Transformations of Terpenes: Part XXIII-Fermentation of Geraniol, Nerol & Limonene by a Soil Pseudomonad," Indian Journal of Biochemistry and Biophysics, 14, pp. 288-291 (1977).
Madyastha et al, "Biodegradation of Acetates of Geraniol, Nerol & Citronellol by P. Incognita: Isolation & Identification", Indian Journal of Biochemistry and Biophysics 20, pp. 136-140 (6-1983).
Chakrabarty et al., Proc. Nat. Acad. Science, USA, 70, No. 4, 1137-1140. 1973.
Bensen et al., J. of Bacteriology, 126, 794-798 (1976).
Pemberton et al., Nature, 268, 732-733 (1977).
Bensen et al., J. of Bacteriology, 132, 614-621 (1977).
Vandenbergh et al, Applied and Environmental Microbiology, 42, 737-739 (1981).
Seubert W. in J. Bacteriology, 79, 426-434 (1960).
Cantwell et al., in J. Bacteriology, 135, 324-333 (1978).
Hansen and Olsen, Nature (London) 274, 715-717 (1978).
Stanier et al., The Aerobic Psuedomonads: A Taxonomic Study, J. Gen. Microbiol., 43, 159-271 (1966).
Olsen, J., Bacteriology, 133, 210-216 (1978).
Davis et al., Cold Spring Harbor Laboratory, Cold Spring Harbor, NY (1980).
Vandenbergh et al., Appl. Environ. Microbiol, 45(6), pp. 1953-1955 (1983).

Primary Examiner—Thomas G. Wiseman
Assistant Examiner—John E. Tarcza
Attorney, Agent, or Firm—Ian C. McLeod

[57] ABSTRACT

A bacterial method and compositions for degrading isoprenoids using selected Pseudomonas strains, particularly strains of Pseudomonas putida, are described. Plasmid pSRQ50 in the selected Pseudomonas strains was isolated from an isoprenoid rich environment. pSRQ50 is not naturally transmissible by conjugation and was found to encode for isoprenoid degradation. In addition, a method and compositions utilizing vector plasmid pRO1742 (pRO1600:Tn904) or other Tn904 containing vectors for transferring pSRQ50 and other transfer related plasmids by conjugal mating is described. Isoprenoids, such as citronellol and geraniol, from citrus wastes are degraded by the Pseudomonas strains.

27 Claims, 1 Drawing Figure

BACTERIAL METHOD AND COMPOSITIONS FOR ISOPRENOID DEGRADATION

BACKGROUND OF THE INVENTION

(1) Field of the Invention

The present invention relates to isoprenoid degrading Pseudomonas strains including plasmid pSRQ50 which encodes for the degradation. In particular, the present invention relates to *Pseudomonas putida* strains containing plasmid pSRQ50 and to an improved degradation method using such strains.

(2) Prior Art

The prior art has described various Pseudomonas strains which degrade aliphatic and aromatic compounds. In some instances the degradation is encoded by genes on a chromosome and in other instances by genes on a plasmid. Examples of such Pseudomonas strains are described by Chakrabarty et al. Proc Nat Acad Science USA 70 No. 4 1137–40 (1973); Bensen et al., J. of Bacteriology 126 794–798, (1976); Pemberton et al., Nature 268 732–733, (1977). Bensen et al., J. of Bacteriology 132 614–621, (1977) and Vandenbergh et al, Applied and Environmental Microbiology 42, 737–739, (1981).

The prior art has also described *Pseudomonas citronellolis* for degrading isoprenoids, particularly Seubert W. in J. Bacteriology 79 426–434 (1960) and Cantwell et al. in J. Bacteriology 135 324–333, (1978). *Pseudomonas citronellolis* ATCC 13674 was surveyed for its extrachromosomal deoxyribonucleic acid (DNA) content, following the procedure of Hansen and Olsen, Nature (London) 274: 715–717 (1978). *P. citronellolis* ATCC 13674 was observed to contain no resident plasmids. The problem with ATCC 13674 is that it has been found to be quite slow in utilizing citronellol as a sole carbon source. The carbohydrates arabinose and melibiose are not metabolized to produce acid which are also distinguishing characteristics.

OBJECTS

It is therefore an object of the present invention to provide Pseudomonas strains which have an improved ability to degrade isoprenoid compounds and a method for the use thereof. It is further an object of the present invention to describe a method for the transfer of plasmids which encode for isoprenoid degradation or other transfer related plasmids. These and other objects will become increasingly apparent by reference to the following description and to FIG. 1.

IN THE DRAWINGS

FIG. 1 shows an agarose gel electrophoresis analysis of CsCl-ethidium bromide-purified DNA preparations derived from various strains. The agarose concentration was 0.7%, and migration was from top to bottom. (A) Parental strain *Pseudomonas putida* PPU2. (pSRQ80/pSRQ50); form the top to the bottom bands are 80-Mdal covalently closed circular (CCC) DNA: CCC band of the 50-Mdal plasmid; and the fragmented chromosomal DNA band. (B) *Pseudomonas putida* PPO2011 (pRO1742/pSRQ80/pSRQ50); 80-Mdal CCC DNA band; 50-Mdal/CCC plasmid band; fragmented chromosomal DNA band; and the 10.6 Mdal dimer of pRO1742. (C) *Pseudomonas aeruginosa* PA02(-pRO1742); faint fragmented chromosomal band; and the CCC band of the 5.4 Mdal plasmid (pRO1742). (D) *Pseudomonas putida* PPO208 (pSRQ50); the 50-Mdal CCC DNA band; and faint fragmented chromosomal band.

GENERAL DESCRIPTION

The present invention relates to an improvement in the method for the degradation of isoprenoid compounds with a bacterium of the genus Pseudomonas, which comprises: degrading an isoprenoid with a strain of *Pseudomonas putida* containing the plasmid pSRQ50. The isoprenoid concentration is usually less than about 0.5 percent by weight to allow growth.

Further the present invention relates to a composition which comprises at least about $10^8$ CFU per ml of a *Pseudomonas putida* containing the plasmid pSRQ50 as carried in *Pseudomonas putida* NRRL-B-15175. To be practically useful, the composition to be supplied to users contains at least about $10^8$ CFU per ml up to about $10^{14}$ CFU per ml. Such compositions are not naturally occurring and generally include nitrogen, carbohydrate and mineral nutrients for the bacteria and preservation agent to maintain viability of the bacteria. The composition can be in preserved form such as lyophilized or frozen as is well known to those skilled in the art. The compositions can include other bacteria such as other organic compound utilizing strains, particularly Pseudomonas strains as are known to those skilled in the art.

The plasmid pSRQ50 does not transfer by conjugation without a means for facilitating the transfer. Thus the present invention also relates to the method of indirectly transferring at least one resident plasmid which resists conjugal transfer, such as pSRQ50, in a first Pseudomonas to a second Pseudomonas which comprises:

(a) providing by transformation in the first Pseudomonas a vector plasmid aggregated with transposon Tn904 along with the resident plasmid to produce a transformant bacterium; and (b) conjugally mating the transformant bacterium with the second Pseudomonas to transfer the resident plasmid from the first to the second Pseudomonas to produce a transconjugant bacterium with the plasmid. Finally the present invention relates to the plasmid aggregation pRO1742/pSRQ50 as carried in *Pseudomonas putida* NRRL-B-15174 and certain newly created strains.

SPECIFIC DESCRIPTION

The initial isolation of a Pseudomonas putida strain which is able to degrade citronellol or geraniol as sole sources of carbon and energy is described. The presence of plasmid pSRQ50 which encodes for degradation of these compounds is also described.

EXAMPLE 1

Soil samples were obtained surrounding a waste treatment lagoon from a citrus pulping facility which had been in operation for many years. The soil samples were used as an inoculant for liquid culture enrichment and were incubated for 72 hours at 25° C. in a minimal salts medium (mmo) (Stanier et al., The Aerobic Pseudomonads: a taxonomic study. J. Gen. Microbiol. 43 159–271 (1966). The medium contained a specific acyclic isoprenol carbon source (0.2%) and yeast extract (0.05%). After incubation, portions of the enrichments were plated onto agar (mmo) which contained a specific acyclic isoprenol carbon source. A strain was obtained that was able to utilize citronellol or geraniol as its sole carbon and energy source. The strain was purified and identified as *Pseudomonas putida* NRRL-B-15169 (PPU2.) as shown in Table 1.

NRRL-B-15168 (PPU1.) was also found which did not degrade geraniol.

TABLE 1

List of Bacteria Strains

| Strains | Relevant Phenotype | | Deposit |
|---|---|---|---|
| *Pseudomonas putida* PPU1. | Prototroph | | NRRL-B-15168 |
| *Pseudomonas putida* PPU2.(pSRQ80/pSRQ50) | Prototroph | | NRRL-B-15169 |
| *Pseudomonas putida* PPU2.4(pSRQ80/pSRQ50) | his- | | NRRL-B-15170[b] |
| *Pseudomonas putida* PPU2.6(pSRQ80/pSRQ50) | trp- | | NRRL-B-15171[c] |
| *Pseudomonas putida* PPO208[a] | trp- | | NRRL-B-15172[c] |
| *Pseudomonas putida* PPO2011[a] | his- | | NRRL-B-15173[b] |
| *Pseudomonas aeruginosa* PAO2(pRO1742)[a] | ser- | containing (pRO1742) | NRRL-B-15176[d] |
| *Pseudomonas putida* PPO2011(pRO1742/pSRQ80/ pSRQ50) | his- | containing (pRO1742) | NRRL-B-15174[b] |
| *Pseudomonas putida* PPO208(pSRQ50) | trp- | containing (pSRQ50) | NRRL-B-15175[c] |

[a] From Dr. Ronald H. Olsen, University of Michigan
[b] Histidine requiring auxotroph
[c] Tryptophan requiring auxotroph
[d] Serine requiring auxotroph

*Pseudomonas putida* NRRL-B-15169 PPU2. was surveyed for its extrachromosomal deoxyribonucleic acid (DNA) content, following the procedure of Hansen and Olsen, Nature (London) 274, 715–717 (1978). This isolate was found to contain 80-Mdal and 50-Mdal resident plasmids, designated as pSRQ80 and pSRQ50, respectively.

EXAMPLE 2

Conjugal mating experiments were accomplished according to the general method of Olsen, J. of Bacteriology 133, 210–216 (1978) using vector plasmid pRO1742 which is pRO1600 aggregated with transposon Tn904 as described in a U.S. Patent Application Ser. No. 488,036 recently filed by Ronald H. Olsen on April 25, 1983 and assigned to a common assignee. The plasmid derivatives of pRO1600 are described in U.S. application Ser. No. 147,563, filed May 8, 1980 by Ronald H. Olsen, now U.S. Pat. No. 4,374,200. The donors were auzotrophs obtained through mutagenesis with 1-methyl-3-nitro-1-nitrosogunaidine (NTG) (Sigma Chemical Co., St. Louis, MO), according to the method described in Vandenbergh et al. Appl. Environ. Microbiol (submitted) (1982).

The strains *Pseudomonas putida* PPU2.4 (pSRQ80/pSRQ50) and PPU2.6 (pSRQ80/pSRQ50) were plate mated with *Pseudomonas putida* PPO208 and PPO2011, respectively. The recipients PPO208 and PPO2011 are plasmid free strains which can not utilize citronellol and geraniol as sole source of carbon and energy. The initial plate matings were unsuccessful using direct selection. Broth mating were also attempted and unsuccessful, showing that the plasmid resists transfer.

*Pseudomonas putida* PPU2.6 (pSRQ80/pSRQ50) was then transformed with a 5.4-Mdal vector plasmid pRO1742 (pRO1600 Tn904) according to the general procedure of Davis et al. Cold Spring Harbor Laboratory, Cold Spring Harbor, NY (1980). The plasmid pRO1742 contains the streptomycin resistance transposon Tn904 as described in the application filed by Ronald H. Olsen. The transformant, *P. putida* PPU2.6 (pRO1742/pSRQ80/pSRQ50) appeared at a frequency of $1 \times 10^3$ transformants per microgram of DNA, was checked for expression of all markers and used as donors in plate matings with *P. putida* PPO2011.

Plate mating experiments were accomplished at 25° C. using minimal media (mmo) supplemented with histidine, streptomycin and geraniol as the sole carbon and energy source. The transconjugant from these plate matings, *P. putida* NRRL-B-15174 PPO2011 (pRO1742/pSRQ80/pSRQ50), was able to utilize geraniol and citronellol as sole carbon and energy sources as shown in Table 2.

TABLE 2

Nutritional Properties of Wild-Type Strain and Derived Strains[a].

| | Growth Carbon Source | |
|---|---|---|
| Strain Designation | Citronellol | Geraniol |
| *Pseudomonas putida* PPU1. | + | − |
| *Pseudomonas putida* PPU2.(pSRQ80/pSRQ50) | + | + |
| *Pseudomonas putida* PPU2.(pSRQ80/pSRQ50) | + | + |
| *Pseudomonas putida* PPO2011(pRO1742/pSRQ80/pSRQ50) | + | + |
| *Pseudomonas putida* PPO208(pSRQ50) | + | + |
| *Pseudomonas putida* PPO2011 | − | − |
| *Pseudomonas putida* PPO208 | − | − |

[a] Incubation was for 72 hours at 25° C. Volatile carbon sources were incorporated directly into the medium as well as in the vapor phase in a sealed container.
+ = Growth
− = No growth This strain was examined for extrachromosomal DNA content and contained pSRQ80, pSRQ50 and a 10.6 Mdal dimer of pRO1742 as shown in FIG. 1. The 10.6 Mdal plasmid coded for streptomycin resistance and through restriction endonuclease digestion with Sst1 was found to have the same Sst1 cleavage sites as pRO1742.

EXAMPLE 3

Citronellol and geraniol were used as the substrates for whole cell oxygen uptake studies comparing the parental strain *P. putida* NRRL-B-15169 PPU2.

(pSRQ80/pSRQ50), with the transconjugant *P. putida* NRRL-B-15174 PPO2011 (pRO1742/pSRQ80/pSRQ50). Oxygen consumption was measured at 25° C. with a model 53 YSI bilogical oxygen monitor and a Clark Fixed Voltage Polarographic probe (Yellow Springs Instrument Co., Yellow Springs, OH). The results indicate similar rates of utilization for both parental and transconjugant strains as shown by Table 3.

TABLE 3

Oxidation of Acyclic Isoprenoids by Various Suspensions of Whole Cells

| Bacterial Strain | $O_2$ Uptake[a] Citronellol | Geraniol |
|---|---|---|
| *Pseudomonas putida* PPU1. | 3.0 | 0.0 |
| *Pseudomonas putida* PPU2.(pSRQ80/pSRQ50) | 8.5[b] | 9.8 |
| *Pseudomonas putida* PPO2011(pRO1742/pSRQ80/pSRQ50) | 9.0 | 6.0 |
| *Pseudomonas putida* PPO208(pSRQ50) | 7.5 | 4.0 |

[a] $\mu l\ O_2/h$ mg dry wt.
[b] These values were corrected for endogeneous oxygen uptake by subtracting the value for a control without substrate.
Reaction mixtures contained 20 mM of substrate.

EXAMPLE 4

*P. putida* NRRL-B-15174 PPO2011 (pRO1742/pSRQ80/pSRQ50) was used as the donor for plate matings with *P. putida* PPO208. The transconjugant *P. putida* NRRL-B-15175 PPO208 (pSRQ50) was obtained. The transconjugant was a tryptophan auxotroph that was able to grow in minimal media containing either citronellol or geraniol as sole carbon and energy source as shown in Table 2. Extrachromosomal DNA content profiles revealed the presence of the 50-Mdal plasmid pSRQ50 as shown in FIG. 1. Whole cell oxygen uptake studies using the strain *P. putida* NRRL-B-15175 PPO208 (pSRQ50) with either citronellol or geraniol as the substrates, revealed similar rates of utilization when compared to the other strains as shown in Table 3.

As can be seen Example 4, *P. putida* PPO2011 and PPO208 isolates, acquired the ability to utilize citronellol or geraniol as sole carbon and energy source, through conjugation with *P. putida* PPU 2.6 (pRO1742/pSRQ80/pSRQ50). These results demonstrate that the strains acquired the ability to degrade these compounds from a plasmid pSRQ50. The strains metabolize the carbohydrates arabinose and melibiose and thus are different from *Pseudomonas citronellolis* ATCC 13674.

EXAMPLE 5

Restriction enzyme digestions of cesium chloride-ethidium bromide purified plasmid DNA using restriction endonuclease Sst1, demonstrated that the plasmid pSRQ50 from *P. putida* PPO208 (pSRQ50) was the same as pSRQ50 observed in the parental strain *P. putida* PPU2.

EXAMPLE 6

Whole cell oxygen uptake studies comparing the parental and transconjugant strains, demonstrated relatively slow utilization rates for citronellol or geraniol compared to glucose (13.5 microliters of $O_2$ per hour per mg of dry weight of cells). Similar results were initially observed by Seubert with *Pseudomonas citronellolis* described previously. It was found that *Pseudomonas citronellolis* ATCC 13674 grew in the presence of citronellol as isolated colonies in 48 hours whereas the transconjugants containing pSRQ50 grew within 24 hours and thus were much faster.

Previous work has suggested that the failure of bacteria to utilize acyclic isoprenols was due to the toxic effect of these alcohols. Studies have shown that beta-alkyl branching of the linear alkyl skeletons blocks the beta-oxidation pathway, hence reducing the biodegradation of these environmentally recalcitrant compounds (Cantwell, S. G. et al J. Bacteriol. 79:324–333 (1978)). The present invention provides a method for degrading the isoprenoids more rapidly than the prior art *Pseudomonas citronellolis* ATCC 13674.

EXAMPLE 7

This example shows testing for colonization of bacterial cultures *Pseudomonas putida* NRRL-B-15168 and NRRL-B-15169, when inoculated into a waste lagoon system of a citrus processing plant. Bacterial cultures *Pseudomonas putida* NRRL-B-15168 and NRRL-B-15169 were grown and concentrated. Ten liters of each culture at a concentration of $10^{11}$ CFU/ml, were added to Lagoon A of a citrus processing plant waste system consisting of 3 lagoons connected in series. Lagoon A, Lagoon B, Lagoon C contained approximately $6\times10^6$, $6\times10^6$ and $14\times10^6$ gallons of waste material respectively. The average daily flow through the Lagoon system A, B, C during the evaluation period was $1.1\times10^6$ gallons per day. The inoculum rate was 30 liters of liquid culture per week (total $3\times10^{15}$ CFU). Total viable cell counts were determined from samples taken from Lagoons A, B, C using standard plate count method on differential media selecting for NRRL-B-15168 and NRRL-B-15169. The results are depicted in Table 4. The results indicated that the cultures survived and colonized in high populations in the entire waste lagoon system, even through only Lagoon A was inoculated.

TABLE 4

Total Viable Cell Determination (CFU/ml)

| | Zero[a] | WEEKS AFTER INOCULATION | | | | | |
| | | 1 | 2 | 3 | 4 | 5 | 6 |
|---|---|---|---|---|---|---|---|
| Lagoon A | $<10^2$ | $1.0\times10^3$ | $5.7\times10^5$ | $1.0\times10^4$ | $1.5\times10^5$ | $2.2\times10^4$ | $5.0\times10^3$ |
| Lagoon B | $<10^2$ | $7.0\times10^1$ | $1.3\times10^4$ | $1.3\times10^4$ | $7\times10^3$ | $9.0\times10^3$ | $3.5\times10^2$ |

TABLE 4-continued

| | Total Viable Cell Determination (CFU/ml) | | | | | | |
|---|---|---|---|---|---|---|---|
| | WEEKS AFTER INOCULATION | | | | | | |
| | Zero[a] | 1 | 2 | 3 | 4 | 5 | 6 |
| Lagoon C | $<10^2$ | $<10^2$ | $1.3 \times 10^4$ | $1.0 \times 10^3$ | $9.5 \times 10^2$ | $5.5 \times 10^3$ | $1.0 \times 10^1$ |

[a]Sample taken prior to inoculation.

In this example, *Pseudomonas putida* NRRL-B-15168 was used in order to potentiate the degradative capabilities of *Pseudomonas putida* NRRL-B-15169. In an environment where there are many different carbon sources other bacteria are desirable to insure adequate degradation of the isoprenoids.

EXAMPLE 8

This example shows inoculation of bacterial cultures NRRL-B-15168, NRRL-B-15169 and ATCC 13674 into the waste aeration tanks of a second citrus processing plant, and evaluation for colonization and improvement of waste degradation efficiency.

The second citrus processing plant contained a waste treatment system consisting of three $2 \times 10^6$ gallon aeration tanks and one $1 \times 10^6$ gallon aeration tank. The average daily flow through the system was 904,000 gallons per day during the evaluation period.

Cultures were grown, harvested and concentrated as in Example 7. Total viable cell counts were determined using the method of Example 7. The results are depicted in Table 5. The results indicated that the cultures survived and colonized the entire waste aeration tank system.

During the entire evaluation period, samples were removed and examined for TOC (Total Organic Carbon), COD (Chemical Oxygen Demand) and DO (Dissolved Oxygen). Total tabulation of these parameters are depicted in Table 6.

Table 7 depicts the comparison of COD, TOC, and DO average values obtained during the entire evaluation period to the comparable period of the previous year. As observed in Table 7, the initial COD and TOC values of the input waste were higher, whereas the initial DO was lower than the values recorded in the previous year. Results indicated an 8.0% and 7.4% improvement in the efficiency of COD and TOC reduction in the final effluent, respectively, as compared to previous year. An overall improvement in the waste removal efficiency was obtained when bacterial cultures NRRL-B-15168, NRRL-B-15169 and ATCC 13674 were added to the waste aeration tank system.

In this example *Pseudomonas citronellolis* ATCC 13674 was used along with the strains of Example 7. This strain was used to evaluate compatibility of NRRL-B-15168 and NRRL-B-15169 with other citrus oil degrading strains.

TABLE 5

| | Total Viable Cell Determination (CFU/ml) | | | | |
|---|---|---|---|---|---|
| | WEEKS AFTER INOCULATION | | | | |
| | Zero[a] | 1 | 2 | 3 | 4 |
| Aeration Tank 2 | $<10^2$ | $2.1 \times 10^5$ | $3.0 \times 10^6$ | $3.5 \times 10^6$ | $1.5 \times 10^6$ |
| Aeration Tank 4 | $<10^2$ | $1.5 \times 10^5$ | $1.5 \times 10^5$ | $2.1 \times 10^5$ | $6.0 \times 10^6$ |

[a]Sample taken prior to inoculation

TABLE 6

COD & TOC ppm Values for Tank 2, Tank 4, and Effluent During Test Period.

| INPUT FLOW (DO) mqpd | COD (DO) ppm | | | TOC ppm | | |
|---|---|---|---|---|---|---|
| | TANK 2 | TANK 4 | FINAL EFFLUENT | TANK 3 | TANK 4 | FINAL EFFLUENT |
| 1.390(6.0) | 7820(0.5) | 5940(0.3) | 1290 | 2895 | 2200 | 515 |
| .7957(6.5) | 6330(0.7) | 5910(0.5) | 1980 | 2345 | 2190 | 790 |
| 1.430(5.4) | 7150(0.7) | 5490(0.3) | 1060 | 2750 | 2110 | 425 |
| 1.061(6.5) | 6120(2.2) | 6210(2.5 | 820 | 2350 | 2390 | 328 |
| 1.052(2.9) | 7330(4.9) | 5900(5.4) | 658 | 2820 | 2270 | 263 |
| 1.448(5.2) | 5798(0.7) | 5395(1.5) | 810 | 2230 | 2075 | 324 |
| 1.588(3.5) | 6305(0.6) | 5668(0.6) | 863 | 2425 | 2180 | 345 |
| .9469(2.7) | 8580(1.7) | 5330(2.1) | 798 | 3300 | 2050 | 319 |
| .873(3.1) | 7527(1.6) | 6071(2.4) | 500 | 2895 | 2335 | 200 |
| 1.463(1.0) | 6188(0.8) | 6006(0.9) | 470 | 2380 | 2310 | 188 |
| 1.127(3.1) | 5733(0.8) | 4550(1.4) | 455 | 2205 | 1750 | 182 |
| .462(1.0) | 7750(0.8) | 4490(2.8) | 488 | 2980 | 1725 | 195 |
| 1.343(2.8) | 5551(0.7) | 4836(0.7) | 375 | 2135 | 1860 | 150 |
| UNK | 6253(0.4) | 4953(2.5) | 348 | 2405 | 1905 | 139 |
| 1.454(0.9) | 4953(0.2) | 5005(0.4) | 1188 | 1905 | 1925 | 475 |
| .6167(3.3) | 7709(0.7) | 5343(1.1) | 318 | 2965 | 2055 | 127 |
| .767(3.4) | 6617(1.7) | 2808(2.1) | 290 | 2545 | 1080 | 116 |
| .643(3.2) | 6620(0.8) | 4420(2.2) | 198 | 2545 | 1700 | 76 |
| 1.831(6.3) | 4660(1.1) | 4250(1.3) | 222 | 1790 | 1635 | 89 |
| .505(6.6) | 5670(1.2) | 2700(0.9) | 192 | 2180 | 1040 | 74 |
| 1.172(6.6) | 5109(0.7) | 1105(1.8) | 200 | 1965 | 425 | 80 |
| .606(6.2) | 4810(1.9) | 195(2.6) | 155 | 1850 | 75 | 62 |
| 1.180(6.9) | 4860(0.5) | 3930(3.7) | 185 | 1870 | 1510 | 74 |
| .413(2.4) | 4550(3.0) | 200(2.4) | 205 | 1820 | 80 | 82 |
| .641(3.1) | 4550(0.7) | 3900(2.3) | 226 | 1750 | 1500 | 87 |
| .903(2.9) | 4340(0.9) | 3900(2.1) | 228 | 1670 | 1500 | 91 |
| .454(1.1) | 4705(0.4) | 390(0.6) | 200 | 1810 | 150 | 77 |
| .267(5.8) | 4795(2.0) | 130(2.1) | 175 | 1845 | 50 | 70 |
| .480(2.5) | 4330(0.6) | 4520(2.7) | 138 | 1665 | 1740 | 55 |
| .308(2.6) | 4580(0.6) | 4330(2.6) | 223 | 1760 | 1665 | 89 |

TABLE 6-continued

COD & TOC ppm Values for Tank 2, Tank 4, and Effluent During Test Period.

| INPUT FLOW (DO) mqpd | COD (DO) ppm | | | TOC ppm | | |
|---|---|---|---|---|---|---|
| | TANK 2 | TANK 4 | FINAL EFFLUENT | TANK 3 | TANK 4 | FINAL EFFLUENT |
| .402(6.2) | 4060(0.7) | 2160(4.0) | 195 | 1560 | 830 | 78 |
| .354(6.3) | 350(4.3) | 160(6.0) | 205 | 135 | 65 | 82 |
| .960(2.1) | 4490(0.4) | 2940(2.2) | 225 | 1725 | 1130 | 90 |

TABLE 7

Comparison of average COD, DO and TOC values of Tank 2, Tank 4 and Final Effluent during test period and same 60 day period of prior year

| | 60 Day Test Period | Same 60 Day Period Of Prior Year | % Change Compared to Same Period of Prior Year |
|---|---|---|---|
| TOTAL FLOW Million gallons per day | .904 | 1.221 | −26.0% |
| DP of Input | 4.06 | 4.42 | −8.1% |
| TANK 2 COD ppm | 5642 | 4236 | +33.2% |
| DO | 1.20 | 1.74 | −31.0% |
| TANK 4 COD ppm | 3913 | 2204 | +77.5% |
| DO | 2.03 | 2.90 | +30% |
| FINAL COD ppm | 481 | 692 | −30.5% |
| EFFLUENT DO | 3.43 | 3.21 | +6.9% |
| % Efficiency Removal of COD | 91.5 | 83.7 | +7.8% |
| TANK 2 TOC ppm | 2166 | 1618 | +33.9% |
| TANK 4 TOC ppm | 1500 | 832 | +80.3% |
| FINAL EFFLUENT TOC ppm | 192 | 261 | −26.4% |
| % Efficiency Removal of TOC | 91.1 | 83.9 | +7.2% |

It was also observed that the utilization of geraniol by *P. putida* NRRL-B-15169 is not via the typical alkane utilization pathway as previously observed by Bensen et al., J. of Bacteriology 126 794–798, (1976). Enzyme assays conducted utilizing a geraniol and 1-octanol as substrates, demonstrate that *P. putida* NRRL-B-15169 did not possess a typical alcohol dehydrogenase requiring NAD as observed with the OCT plasmid of Bensen et al.

It will be recognized that the various strains herein can be easily mutated to other auxotrophs or prototrophs by mutation means well known to those skilled in the art. It is intended that the claims herein include prototrophs or auxotrophs, particularly amino acid requiring auxotrophs.

I claim:

1. The method for the degradation of isoprenoid compounds with a bacterium of the genus Pseudomonas which comprises:
    (a) degrading an isoprenoid with a strain of *Pseudomonas putida* containing the plasmid pSRQ50 as carried in *Pseudomonas putida* NRRL-B-15169, 15170, 15171, 15174 or 15175, wherein the Pseudomonas has been cultured prior to being added to the isoprenoid to produce the degradation.

2. The method of claim 1 wherein the Pseudomonas contains plasmids pSRQ50 and pSRQ80 as carried in *Pseudomonas putida* NRRL-15169.

3. The method of claim 1 wherein the Pseudomonas contains plasmids pSRQ50, pSRQ80 and pRO1742 as carried in *Pseudomonas putida* NRRL-B-15174.

4. The method of claim 1 wherein the Pseudomonas is *Pseudomonas putida* NRRL-B-15171 and prototrophs or auxotrophs thereof, differing from NRRL-B-15171 only in non-essential compounds which are metabolized.

5. The method of claim 1 wherein the Pseudomonas contains the plasmid pSRQ50 as carried in *Pseudomonas putida* NRRL-B-15175 without other plasmids.

6. The method of claim 1 wherein the Pseudomonas is *Pseudomonas putida* NRRL-B-15169 and auxotrophs thereof, differing from NRRL-B-15169 only in non-essential compounds which are metabolized.

7. The method of claim 1 wherein the Pseudomonas is NRRL-B-15175 and prototrophs and auxotrophs thereof, differing from NRRL-B-15175 only in non-essential compounds which are metabolized.

8. The method of claim 1 wherein the Pseudomonas is *Pseudomonas putida* NRRL-B-15174 and prototrophs and auxotrophs thereof, differing from NRRL-B-15174 only in non-essential compounds which are metabolized.

9. The method of claim 1 wherein the Pseudomonas is *Pseudomonas putida* NRRL-B-15170 and prototrophs and auxotrophs thereof, differing from NRRL-B-15170 only in non-essential compound which are metabolized.

10. The method of claim 1 wherein the strain of *Pseudomonas putida* containing pSRQ50 is combined with other Pseudomonas.

11. The method of claim 10 wherein the other Pseudomonas is *Pseudomonas putida* NRRL-B-15168.

12. The method of claim 11 wherein the other Pseudomonas is in addition *Pseudomonas citronellolis* ATCC 13674.

13. A biologically pure culture of a *Pseudomonas putida* containing the plasmid pSRQ50 as carried in *Pseudomonas putida* NRRL-B-15175.

14. The composition of claim 13 wherein the *Pseudomonas putida* is NRRL-B-15169 or auxotrophs thereof, differing from NRRL-B-15169 only in non-essential compounds which are metabolized.

15. The composition of claim 13 wherein the *Pseudomonas putida* is NRRL-B-15170 or 15171 and prototrophs and auxotrophs thereof, differing from NRRL-B-15170 or 15171 only in non-essential compounds which are metabolized.

16. The composition of claim 13 wherein the *Pseudomonas putida* is NRRL-B-15174 and prototrophs and auxotrophs thereof, differing from NRRL-B-15174 only in non-essential compounds which are metabolized.

17. The composition of claim 13 wherein the *Pseudomonas putida* is NRRL-B-15175 and prototrophs and auxotrophs thereof, differing from NRRL-B-15175 only in non-essential compounds which are metabolized.

18. The plasmid aggregation pRO1742 pSRQ50 as carried in *Pseudomonas putida* NRRL-B-15174 maintained separately.

19. The plasmid aggregation of claim 18 including the plasmid pSRQ80.

20. The method of indirectly transferring at least one resident plasmid which encodes for isoprenoid degradation in a first Pseudomonas to a second Pseudomonas which comprises:
  (a) providing in the first Pseudomonas a vector plasmid aggregated with transposon Tn904 along with the resident plasmid by transformation to produce a transformant bacterium; and
  (b) mating the transformant bacterium with the second Pseudomonas to transfer the resident plasmid to the second Pseudomonas to produce a transconjugant bacterium.

21. The method of claim 20 wherein the vector plasmid is pRO1742 as carried in *Pseudomonas aeruginosa* NRRL-B-15176.

22. The method of claim 21 wherein the resident plasmid is pSRQ50 as carried in *Pseudomonas putida* NRRL-B-15170.

23. The method of claim 21 wherein the resident plasmid is pSRQ50.

24. The method of claim 21 wherein the resident plasmid is pSRQ50 as carried in *Pseudomonas putida* NRRL-B-15175.

25. The method of claim 20 wherein the resident plasmid is pSRQ50 along with pSRQ80 and pRO1742 as carried in *Pseudomonas putida* NRRL-B-15174.

26. A bacterium which comprises *Pseudomonas putida* NRRL-B-15175 and auxotrophs and prototrophs thereof, differing from NRRL-B-15175 only in nonessential compounds which are metabolized.

27. A bacterium which comprises *Pseudomonas putida* NRRL-B-15174 and auxotrophs and prototrophs thereof, differing from NRRL-B-15174 only in nonessential compounds which are metabolized.

* * * * *

UNITED STATES PATENT AND TRADEMARK OFFICE
CERTIFICATE OF CORRECTION

PATENT NO. : 4,593,003
DATED : June 3, 1986
INVENTOR(S) : Peter A. Vandenbergh

It is certified that error appears in the above-identified patent and that said Letters Patent are hereby corrected as shown below:

Column 1, line 58 "form" should be --from--.

Column 1, line 63 "50-Mdal/CCC" should be --50-Mdal CCC--.

Column 3, line 57 "auzotrophs" should be --auxotrophs--.

Column 4, line 46, Table 2, line 3 "Pseudomonas putida PPU2.(. ." should be --Pseudomonas putida PPU2.6(. .--.

Column 5, line 40 after "seen", --from-- should be inserted.

Column 6, line 60 "through" should be --though--.

Column 8, line 46, Table 6, line 4 "6210(2.5" should be --6210(2.5)--.

Column 10, line 40 "compound" should be --compounds--.

Signed and Sealed this

Sixteenth Day of December, 1986

Attest:

DONALD J. QUIGG

Attesting Officer     Commissioner of Patents and Trademarks